United States Patent [19]

Shaer

[11] Patent Number: 4,518,694

[45] Date of Patent: May 21, 1985

[54] AQUEOUS COMPOSITIONS CONTAINING STABILIZED ENZYMES

[75] Inventor: Elias H. Shaer, Cincinnati, Ohio

[73] Assignee: The Drackett Company, Cincinnati, Ohio

[21] Appl. No.: 414,552

[22] Filed: Sep. 3, 1982

Related U.S. Application Data

[63] Continuation of Ser. No. 173,779, Jul. 30, 1980, abandoned.

[51] Int. Cl.³ .............................................. C12N 9/96
[52] U.S. Cl. ................................ 435/188; 252/174.12
[58] Field of Search ................... 435/188; 252/174.12, 252/DIG. 12

[56] References Cited

U.S. PATENT DOCUMENTS 3,869,399 3/1975 Collins ................................ 252/118
4,287,082 9/1981 Tolfo ............................... 252/174.12
4,318,818 3/1982 Letton ............................ 252/174.12

OTHER PUBLICATIONS

Christensen et al., "Proteolytic Enzymes and Non-Built Liquid Detergents", 55 J. Am. Oil Chemists' Soc., 109–113, (Jan. 1978).

Primary Examiner—Hiram H. Bernstein
Attorney, Agent, or Firm—Charles Zeller

[57] ABSTRACT

Aqueous enzyme preparation stabilized with a salt of a lower molecular weight acid in the presence of alcohol.

19 Claims, No Drawings

AQUEOUS COMPOSITIONS CONTAINING STABILIZED ENZYMES

This is a continuation of application Ser. No. 173,779, filed July 30, 1980, now abandoned.

DESCRIPTION

Background of the Invention

This invention relates to long term stabilization of an enzyme contained in an aqueous composition by a salt of a lower molecular weight organic acid.

The desirability of using enzymes of the proteolytic and alpha amylolytic type in cleaning compositions is well known. These enzymes are useful for their ability to reduce macromolecules such as proteins and starches into smaller molecules so that they can be readily washed away by detergents and/or water. Specifically, the proteolytic enzymes are useful in breaking down proteins and the alpha amylolytic enzymes are useful in breaking down carbohydrates. Detergent compositions containing these enzymes have a wide variety of uses in that they are capable of removing proteinaceous and starchy stains such as egg stains, blood stains, gravy stains and the like.

Detergent compositions containing enzymes have been commercially available in dry powdered form. However, there are inherent problems with these compositions. First, they must be stored in such a way as to be protected from humidity and high heat to insure enzyme stability. Second, these dry powdered compositions are not well suited for several useful applications such as spot cleaners, laundry pre-soaks and pre-spotters which require direct application to the stained surface. For those and other applications it is desirable to have a liquid enzyme composition. Further for economic as well as processing considerations it is advantageous to include significant amounts of water in liquid enzyme compositions. However, there is an inherent problem in adding significant amounts of water to an enzyme containing composition. This is due to the fact that enzymes are inherently unstable in the presence of water resulting in a rapid decrease of enzymatic activity, i.e., the ability of the enzyme to effectively reduce macromolecules into smaller molecules. It is speculated that the loss in enzymatic activity is due to the hydrolyzing action of water on the enzyme.

Further decreases in enzymatic activity will also result from exposing the aqueous enzyme containing compositions to temperatures in excess of 70° C. In fact, if these compositions are exposed to these temperatures for more than a few hours, complete deactivation will occur.

Therefore, in order to have an aqueous based enzyme containing composition which is suitable for the uses described above, it is clear that the enzyme must not only remain stable in water, i.e. retain its enzymatic activity, but it must also be capable of maintaining such stability for extended periods of time at elevated temperatures. For, it is not uncommon to have commercial products stored in warehouses for a period of time before being sold to consumers, where the temperatures during storage far exceeds those of normal room temperature.

Various attempts have been made to stabilize enzymes contained in acqueous compositions. The following are exemplary of these.

U.S. Pat. No. 3,296,094 to Cayle utilizes a partially hydrolyzed and solubilized collagen, and glycerol to stabilize an aqueous proteolytic enzyme composition. The amount of glycerol required for stabilization in this composition is between 35% to 60% by weight of the total composition.

U.S. Pat. No. 3,557,002 to McCarthy utilizes a monohydroxyl alcohol or an alkoxy alcohol to stabilize a proteolytic enzyme. Although the amount of alcohol used in this composition is less than that used in Cayle the residual activity of the enzyme of this composition decreases after long periods of storage at relatively high temperatures.

U.S. Pat. No. 4,169,817 to Weber utilizes either water soluble salts such as sodium or potassium sulfates or chlorides and/or glycerol or alkylene glycols to stabilize a proteolytic enzyme in compositions containing ionic builders and surfactants. Again, significant amounts of glycerol and/or other solids are required to maintain long term enzyme stability in these compositions.

U.S. Pat. No. 3,682,842 to Innerfield utilizes an enzyme-ion binding agent such as trichloroacetic acid or tungstic acid; a salt, such as sodium chloride or ammonium sulfate; an organic solvent such as ethanol; and an anionic surfactant to stabilize a mixture of protolytic and amylolytic enzymes.

U.S. Pat. No. 3,676,374 to Zaki et al. utilizes a mixture of alkane sulfonates or alphaolefin sulfonate compounds, along with an alkyl alkyleneoxy hydroxyl or sulfate compounds to stabilize a proteolytic enzyme in a liquid detergent composition containing water. Additionally, various stabilizing agents can be employed with these compositions such as the water-soluble calcium and magnesium chloride lactates and acetates.

In my application, Ser. No. 023,363 filed Mar. 23, 1979, now U.S. Pat. No. 4,243,546. I disclosed that enzymes could be stabilized in an aqueous medium for long periods of time by adding to the composition an alkanolamine and an organic acid. I have now found that enzyme stability can be maintained in an aqueous medium containing small amounts of alcohol by adding an alkanolammonium salt of a lower molecular weight organic acid or by adding an ammonium or alkali metal salt of such acids.

SUMMARY OF THE INVENTION

It is an object of this invention to provide aqueous based compositions containing stabilized enzymes which are suitable for use as cleaners where the enzymes will be stabilized, i.e. maintain their activity, for long periods of time. It is a further object of this invention to provide such stability by using small amounts of a relatively inexpensive stabilizing agent.

The compositions of this invention require only minor amounts of an enzyme stabilizing agent and an alcohol to achieve superior long term enzyme stability which will be maintained even at elevated temperatures. These compositions are particularly effective as cleaning preparations in a wide range of applications.

The compositions of this invention are comprised of the following ingredients (all amounts given below and throughout this application are on a weight basis):

(a) from about 0.01% to 15% of an enzyme stabilizing agent which is an alkali metal, ammonium, or alkanolammonium salt of a lower molecular weight organic acid selected from the group consisting of formic, acetic, propionic, butyric and valeric acids;

(b) from about 0.006% to about 5% of an enzyme selected from the group consisting of proteases, alpha amylases and mixtures thereof;

(c) from about 1% to about 25% of an alcohol selected from the group consisting of alcohols having the formula ROH wherein R is an alkyl residue of one to six carbon atoms; and (d) from about 10% to about 90% water.

DETAILED DESCRIPTION OF THE PREFERRED EMBODIMENT

In accordance with the present invention, it has been found that the alkali metal, alkanolammonium, or ammonium salts of certain lower molecular weight organic acids, can in the presence of a lower molecular weight monohydroxy alcohol stabilize proteolytic or amylolytic enzymes or mixtures thereof in an aqueous medium. Further, it has been found that the enzyme thus stabilized will retain its activity for an extended period of time, in the order of one year to eighteen months.

The main ingredients of the compositions of this invention are water, enzymes, stabilizing agents and an alcohol.

Water can comprise from about 10% to about 90% of the total composition of the present invention. Preferably water will be present in amounts ranging from about 40% to about 90% by weight. Although not mandatory deionized water is preferred for use herein.

The enzymes which are stabilized by and therefore suitable for use in the present invention are the proteases, the alpha amylases and mixtures of proteases and alpha amylases.

The proteases which are derived from bacterial or fungal sources can be classified into three different categories: acidic, neutral, and alkaline proteases, all of which are useful herein. Proteases derived from plant and animal sources, although not readily classifiable into the above recited categories, are also useful herein. These enzymes are active in pH's ranging from about 3 to about 11. Optimum activity of these enzymes is generally exhibited in the pH range of about 6 to about 10. The proteases catalyze the hydrolysis of the peptide linkages of proteins, polypeptides and other related compounds. By breaking the peptide bonds of proteins, free amino and carboxy groups are formed which are short chain molecules that can easily be washed away by water and/or a detergent. All categories of proteases enumerated above are useful in this invention, however, those having optimum activity in pH's ranging from about 6 to about 9 are preferred. An example of a preferred protease is a serine protease.

The alpha amylases exhibit optimum activity in the acidic pH ranges. These enzymes catalyze reactions which break starch molecules into shorter chain molecules that are readily washed away by detergents and/or water. The alpha amylases may be obtained from animal sources, cereal grains, or bacterial or fungal sources.

The enzyme ingredient of the present invention can be conveniently added in the form of a commercial enzyme preparation. These are generally sold in a dry powder, solution, or slurry form and are comprised of from about 2% to about 80% of active enzymes in combination with an inert carrier such as sodium or calcium sulfate, sodium chloride, glycerol, nonionic surfactants, or mixtures thereof as the remaining 20% to 98%. Examples of commercial protease preparations which are suitable for use in the compositions of this invention include Savinase, Savinase 8.0 Slurry, Esperase, Esperase 8.0 Slurry and Alcalase from Novo Industri A/S, Copenhagen, Denmark; and High Alkaline Protease, Maxatase P, and Alkaline Protease 201 P from G. B. Fermentation Inc., Des Plaines, Ill. Examples of commercial alpha amylase preparation which can be used herein include Amalase THC from G. B. Fermentation Inc., Des Plaines, Ill.; and Termamyl 60L, and Termamyl 60G from Novo Industri A/S, Denmark. An example of a commercial enxyme preparation containing a mixture of alpha amylases and alkaline proteases which can be used herein is Maxatase from G. B. Fermentation Inc.

The commercial enzyme preparation preferred for use herein is Savinase 8.0 Slurry from Novo Industries, an alkaline proteolytic enzyme preparation obtained fromm the genus Bacillus Subtilis containing about 6% by weight of the enzyme and having an activity of 8 kilo novo units.

Compositions of this invention will stabilize from about 0.006% to about 5.0% of an active enzyme. The amount of enzyme which is preferred is from about 0.006% to about 2.5% by weight.

The stabilizing agents which stabilize the enzymes described above are the alkali metals, ammonium, and alkanolammonium salts of lower molecular weight organic acids such as formic, acetic, propionic, butyric and valeric acids. These agents can be used in effective amounts, ranging from about 0.01% to about 15% by weight of the composition. The preferred ranges for these agents are from about 2% to about 10% by weight of the composition, while the most preferred range is from about 2% to about 6%.

As set forth above, alkanolammonium compounds can be used to form the stabilizing salts of the instant invention. Examples of such useful compounds are monoethanolammonium, diethanolammonium, and triethanolammonium.

The fourth main ingredient of the composition of this invention is alcohol which acts to enhance enzyme stability and which also aids in lowering the viscosity and preventing skinning in the compositions of the instant invention. The alcohols which are suitable for use herein are those having the formula of ROH where R is an alkyl residue having from one to six carbon atoms in either the branched or straight chain configurations. The amount of alcohol which is suitable for use in the composition of this invention ranges from about 1% to about 25% by weight of the composition. The amount which is preferred is from about 4% to about 10% by weight of the composition.

In addition to the essential ingredients described above the compositions of this invention can contain other ingredients such as surfactants of either the nonionic or anionic type, organic solvents, solubilizing compounds and perfumes.

Inclusion of a surfactant of either the nonionic or anionic type is advantageous in that they tend to enhance the enzymatic stability of these compositions, however, more importantly they significantly improve the detergent characteristics of these compositions. The nonionics or anionics may be utilized in amounts ranging from about 1% to about 55% and preferably from about 5% to about 30% by weight of the total composition.

Examples of suitable nonionics include:

(1) Ethoxylated fatty alcohols—having the formula: $RO-(CH_2CH_2O)_nH$ where R is from 8 to 18 carbon atoms and n is an integer of from 1 to 500.

Examples of these are:

(a) the condensation product of 1 mole of an aliphatic alcohol, having from 12 to 13 carbon atoms in either a straight or branched chain configuration, with an average of 6.5 moles of ethylene oxide;

(b) the condensation product of 1 mole of an aliphatic alcohol, having from 12 to 15 carbon atoms in either a straight or branched chain configuration, with 9 moles of ethylene oxide; and (c) the condensation product of 1 mole of an aliphatic alcohol, having between 12 and 15 carbon atoms in either the straight or branched chain configuration, with 3 moles of ethylene oxide.

Examples of (a), (b) and (c) are commercially available from the Shell Oil Company under the trade names of Neodol, Neodol 23-6.5, Neodol 25-9, and Neodol 25-3 respectively.

(2) Ethoxylated fatty acids—having the formula:

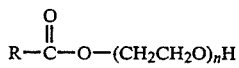

where R and n are as in (1).

(3) Ethoxylated alkyl phenols—having the formula:

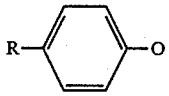

$(CH_2CH_2O)_nH$ where R is an alkyl radical having from 6 to 16 carbons and n is an integer from 1 to 500.

Examples of suitable anionics include:

(1) Soaps—having the formula:

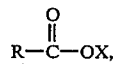

where X is sodium, potassium or ammonium and R is a fatty acid radical either saturated or unsaturated branched or straight chain configuration having from 10 to 18 carbon atoms.

(2) Alkyl benzene sulfonates—having the formula:

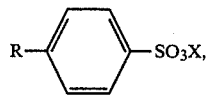

where X is ammonium, triethanol-ammonium, sodium or potassium and R is an alkyl radical having from 8 to 18 carbon atoms.

(3) Hydroxy alkane sulfonates—having the formula:

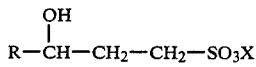

where X is as in (2) and R is an alkyl radical having from 10 to 15 carbon atoms.

(4) Sulfonated fatty acids—having the formula:

where X is as in (2) and n is an integer between 12 and 18.

(5) Sulfonated nonionics—having the formula:

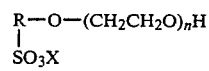

where X is as in (2) and n is an integer from 8 to 16 where R is as in 1.

(6) Fatty alcohol sulfates—having the formula: $CH_3(CH_2)_nCH_2O-SO_3X$ where X is as in (2) and n is an integer from 8 to 16.

(7) Sulfated nonionics—having the formula: $RO-(CH_2CH_2O)_nSO_3X$ where X is as in (2), R is an alkyl radical having from 12 to 18 carbon atoms and n is an integer from 1 to 50.

(8) Mono- and di-esters of sodium sulfosuccinates—having the formula:

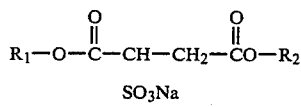

where $R_1$ is either sodium, hydrogen or an alkyl radical having from 1 to 12 carbon atoms. $R_2$ is an alkyl radical having from 1 to 12 carbon atoms.

The surfactants which are preferred are the nonionics of the ethoxylated fatty alcohol type.

The compositions of this invention can also contain organic solvents such as the isoparaffinic mixtures of petroleum distillates. These may be added in amounts of up to 75% by weight with about 10% to about 40% by weight being the amount preferred.

Compositions containing the organic solvents set forth above can also contain solubilizing compounds. Examples of such compounds are the sodium salts of benzene sulfonate, toluene sulfonate, and xylene sulfonate. These agents can be added in amounts of up to about 10% by weight, however about 3% to about 6% by weight of these agents is the preferred amount for inclusion.

In addition to the various ingredients recited above the compositions of this invention can also contain optical brighteners, fabric softeners, anti-static agents, anti-redeposition agents and small amounts of perfume and dye.

The pH of these compositions will generally be around 7, however depending on the enzyme being used the pH can be raised by adding sodium hydroxide or lowered by adding acetic acid.

The various components of the enzyme containing compositions can be mixed together in any order. However, it is preferred that the salt, alcohol and water mixture be prepared first and the enzymes added thereto to prevent any degradation or deactivation of the enzyme. The optional components such as the surfactants can be added at any time.

There are a variety of uses for the compositions of this invention. For example they may be used as spot removers. They may also be used in home laundering operations as pre-soaks and as laundry additives for use during the wash cycle of an automatic washer.

The following examples illustrate the invention.

EXAMPLE 1

The following compositions were prepared and stored in closed-glass containers at 100° F. for the indicated periods of time. It is estimated that one week's storage at 100° F. is equal to between about 2 to 3 months of storage at room temperature.

The pH of each of the following compositions was about 7.

| Ingredients | Sample No. | | | | | | | | | |
|---|---|---|---|---|---|---|---|---|---|---|
| | 1 % wt. | 2 % wt. | 3 % wt. | 4 % wt. | 5 % wt. | 6 % wt. | 7 % wt. | 8[5] % wt. | 9[5] % wt. | 10 % wt. |
| Neodol 25-9[1] | 15 | 15 | 12.5 | 12.5 | 10 | 7.5 | 5 | 15 | 18.25 | 15 |
| Neodol 23-6.5[2] | 15 | 15 | 12.5 | 12.5 | 10 | 7.5 | 5 | 15 | 18.25 | 15 |
| Savinase 8.0[3] Slurry | 1 | 1 | 1 | 1 | 1 | 1 | 1 | 1 | 1 | 1 |
| Sodium Acetate | 4 | 0 | 4 | 6 | 4 | 4 | 4 | 0 | 0 | 2 |
| Sodium Propionate | 0 | 4 | 0 | 0 | 0 | 0 | 0 | 0 | 0 | 0 |
| Ethanol | 7 | 7 | 7 | 5 | 5 | 5 | 5 | 8.8 | 8.8 | 8.0 |
| Water | 58 | 58 | 63 | 63 | 70 | 75 | 80 | 61.6 | 59.1 | 59.1 |
| % Initial Activity | 100 | 100 | 100 | 100 | 100 | 100 | 100 | 100 | 100 | 100 |
| % Act. After[4] 2 Weeks | 97 | 96 | 97 | 97 | 95 | 93 | 92 | | | 95 |
| % Act. After[4] 4 Weeks | 99 | 95 | 97 | 95 | 94 | 94 | 93 | 60 | 63 | 95 |
| % Act. After[4] 6 Weeks | 91 | 88 | 91 | 91 | 88 | 87 | 84 | 51 | 51 | 90 |
| % Act. After[4] 8 Weeks | 93 | 92 | 97 | 91 | 95 | 95 | 89 | | | 88 |

1. Nonionic surfactant comprised of an ethoxylated alcohol where one mole of aliphatic alcohol having from 12 to 15 carbon atoms was ethoxylated with an average of 9 moles of ethylene oxide.

2. Nonionic surfactant comprised of an ethoxylated alcohol where one mole of aliphatic alcohol having from 12 to 13 carbon atoms was ethoxylated with an average of 6.5 moles of ethylene oxide.

3. A commercial alkaline proteolytic enzyme preparation available from Novo Industries containing 6% active enzymes with an activity of 8.0 Kilo Novo protease units.

4. Percent remaining activity was determined by Tri-nitro-benzene sulfonate method using casein as a substrate. Activity values are subject to an experimental error of ±5%.

5. Sample numbers 8 and 9 are not in accordance with the present invention and have been included for the purpose of comparison only.

Review of this data shows that the enzyme will deactivate fairly rapidly as demonstrated by samples 8 and 9 when a stabilizing agent of the present invention is not used. Additionally, as demonstrated by sample No. 10, as little as 2% of one of the stabilizing agents of this invention provides excellent long term stability.

EXAMPLE 2

A composition in accordance with the present invention was prepared, containing 4% by weight of sodium acetate, an enzyme stabilizer salt; 1% by weight of SAVINASE 8.0 Slurry, a commercial enzyme preparation available from Novo Industries; 7% by weight of ethanol; 15% by weight of a nonionic surfactant which is the reaction product of one mole of an aliphatic alcohol having from 12 to 15 carbon atoms with 9 moles of ethylene oxide, available from the Shell Oil Company under the tradename of Neodol 25-9; 15% by weight of a nonionic surfactant which is the reaction product of one mole of an aliphatic alcohol having from 12 to 13 carbon atoms with 6.5 moles of ethylene oxide; 0.25% by weight of a perfume; 0.01% by weight of a dye; and 57.74% by weight of deionized water. This composition was then evaluated for stain removal activity as a prespotter by applying a portion of the composition onto two stained cloths; one cloth containing a stain which was comprised of blood, milk and ink, and a second cloth containing a stain which was dirty motor oil.

After the cloths were treated with the composition they were washed in a commercial detergent composition available from the Procter & Gamble Company under the trademark of Extra Action Tide. Following the wash the stained cloths were allowed to dry and were then analyzed by a Gardener Tri-stimulus color difference meter to determine the percent of the stain which was removed. The percentage of stain removal achieved by prespotting with this composition is given below in column 1.

For purpose of comparison, stained cloths having the same stain as those used above were washed in Extra Action Tide, and then analyzed. The results of this comparative test are given in the table below in column 2.

| Column | 1 | 2 |
|---|---|---|
| Prespotter | This invention | None |
| Stain | | |
| Blood Milk & Ink | 65.0* | 43.2 |
| Dirty Motor Oil | 28.4 | 17.1 |

*all entries in Table represent percent stain removal.

From the above data it is apparent that the compositions of this invention are effective prespotters.

EXAMPLE 3

The composition of this invention which was used as a prespotter in Example 2 was tested as a laundry additive. Again, two stained cloths, one containing a blood, milk and ink stain and a second containing a dirty motor oil stain, were washed separately with approximately 1.2 grams of a commercial detergent composition, Extra Action Tide and approximately 0.75 grams of the composition of Example 2. These washes were conducted in a tergotometer which holds approximately 1 liter of water. After being laundered these stained swatches were allowed to dry and then tested for the percentage of stain removal again by using a Gardener Tri-stimulus color difference meter. The results of this analysis are given in the table below in column 1.

Again, for purposes of comparison, stained clothes having the stains recited above were washed separately in a tergotometer with Extra Action Tide and with a commercial laundry additive containing enzymes BIZ and Extra Action Tide. These were also analyzed for percent stain removal by the method recited above. The results of this analysis are given in columns 2 and 3, respectively.

| Column | 1 | 2 | 3 |
|---|---|---|---|
| Additive | Composition of this invention | None | BIZ |
| Stain | | | |
| Blood Milk & Ink | 44.2* | 20.4 | 8.6 |
| Dirty Motor Oil | 17.8 | 13.4 | 13.9 |

*all results in Table are expressed in terms of percent stain removal.

From the above data, it is apparent that the compositions of this invention are also well suited for use as laundry additives.

Having described some typical embodiment of this invention it is not my intent to be limited to the specific details set forth herein. Rather, I wish to reserve to myself any variations or modifications that may appear to those skilled in the art and fall within the scope of the following claims.

What I claim is:

1. An aqueous-based enzyme containing composition wherein the enzymes have enhanced stability against loss of activity, the composition comprising on a weight basis:
   (a) from about 0 to about 55% of a surfactant selected from the group consisting of anionic and nonionic surfactants, and mixtures thereof;
   (b) from about 0.006 to about 5% of an active enzyme selected from the group consisting of protease and alpha amylase enzymes, and mixtures thereof, said enzyme being provided in pure form or as incorporated within a commercial enzyme preparation comprising from about 2 to about 80% of said enzyme and from about 20 to about 98% of a carrier therefor;
   (c) an enzyme stabilizer consisting essentially of on a weight basis of said composition:
      (i) from about 0.5 to about 15% of a salt of a lower molecular weight organic acid selected from the group consisting of alkali metal, ammonium and alkanol ammonium salts of formic, acetic, propionic, butyric, and valeric acids, and mixtures thereof, and
      (ii) from about 1.0 to about 25% of an alcohol having the formula ROH wherein R is an alkyl having one to six carbon atoms, and
   (d) from about 10 to about 90% water.

2. The composition of claim 1 wherein the carrier is selected from the group consisting of sodium chloride, sodium sulfate, calcium sulfate, glycerol, and combinations of same.

3. The composition of claims 1 or 2 wherein the alkanol ammonium is selected from the group consisting of monoethanolammonium, diethanolammonium and triethanolammonium.

4. The composition of claims 1 or 2 wherein the pH is from about 6 to about 10.

5. The composition of claims 4 wherein the percent by weight of water is from about 40% to about 90%.

6. The composition of claim 5 wherein the percent by weight of the enzyme is from about 0.006% to about 2.5%.

7. The composition of claim 6 wherein the percent by weight of the alcohol is from about 4% to about 10%.

8. The composition of claim 7 wherein the percent by weight of the surfactant is from about 5% to about 30%.

9. The composition of claim 8 wherein the percent by weight of the salt is from about 2% to about 6%.

10. The composition of claim 9 wherein the pH is from about 6 to about 9.

11. The composition of claim 10 wherein the enzyme is a proteolytic enzyme obtained from the Bacillus Substilis.

12. The composition of claim 11 wherein the salt is sodium acetate or sodium propionate.

13. The composition of claim 12 wherein the alcohol is ethanol.

14. The composition of claim 13 wherein the percent by weight of the surfactant is about 30%; and wherein the surfactant is a mixture comprised of about 33.3% by weight of an anionic surfactant and about 66.6% by weight of a nonionic surfactant.

15. The composition of claim 13 wherein the nonionic surfactant is an ethoxylated fatty alcohol having the formula RO—$(CH_2CH_2O)_n$H wher R is from 8 to 18 carbon atoms and n is an integer from 1 to 500.

16. The composition of claim 15 wherein the nonionic surfactant is a mixture of:
   a. the condensation product of 1 mole of an aliphatic alcohol having from 12 to 13 carbon atoms in either a straight or branched chain configuration, with an average of 6.5 moles of ethylene oxide; and
   b. the condensation product of 1 mole of an aliphatic alcohol, having from 12 to 15 carbon atoms in either a straight or branched chain configuration, with 9 moles of ethylene oxide.

17. The composition of claim 16 wherein the nonionic surfactant mixture is comprised of about 50% by weight of component a and about 50% by weight of component b.

18. The composition of claim 17 further comprising by weight of the composition:
   a. from about 1% to about 10% of a solubilizing compound; and
   b. from about 1% to about 75% of an isoparaffinic mixture of petroleum distallates having an average molecular weight of about 154.

19. The composition of claim 18 wherein the solubilizing agent is about 3%–6% by weight of the composition; wherein the isoparaffinic mixture of petroleum distallates is about 10%–40% by weight of the total composition and wherein the solubilizing agent is sodium xylene sulfonate.

* * * * *

UNITED STATES PATENT AND TRADEMARK OFFICE
CERTIFICATE OF CORRECTION

PATENT NO. : 4,518,694
DATED : May 21, 1985
INVENTOR(S) : Elias H. Shaer

It is certified that error appears in the above–identified patent and that said Letters Patent are hereby corrected as shown below:

Cover sheet of patent, Section [45], should read as follows:

[45] Date of Patent:  *May 21, 1985

Cover sheet of patent, between Section [73] and Section [21], should read as follows:

[*] The portion of the term of this patent subsequent to January 6, 1998 has been disclaimed.

Signed and Sealed this

Tenth Day of December 1985

[SEAL]

Attest:

DONALD J. QUIGG

Attesting Officer

Commissioner of Patents and Trademarks

REEXAMINATION CERTIFICATE (711th)

United States Patent [19]

Shaer

[11] B1 4,518,694

[45] Certificate Issued Jun. 30, 1987

[54] AQUEOUS COMPOSITIONS CONTAINING STABILIZED ENZYMES

[75] Inventor: Elias H. Shaer, Cincinnati, Ohio

[73] Assignee: The Drackett Company, Cincinnati, Ohio

Reexamination Request:
No. 90/001,007, May 12, 1986

Reexamination Certificate for:
Patent No.: 4,518,694
Issued: May 21, 1985
Appl. No.: 414,552
Filed: Sep. 3, 1982

Related U.S. Application Data

[63] Continuation of Ser. No. 173,779, Jul. 30, 1980, abandoned.

[51] Int. Cl.$^4$ ............................................... C12N 9/96
[52] U.S. Cl. ................................. 435/188; 252/174.12
[58] Field of Search ................. 252/174.12, DIG. 12; 435/188

[56] References Cited

U.S. PATENT DOCUMENTS

| | | |
|---|---|---|
| 3,557,002 | 1/1971 | McCarty . |
| 3,630,929 | 12/1971 | van Dijk . |
| 3,634,266 | 1/1972 | Theile et al. . |
| 3,676,374 | 7/1972 | Zaki et al. . |
| 3,819,528 | 6/1974 | Berry . |
| 3,869,399 | 3/1975 | Collins .............................. 252/118 |
| 3,920,586 | 11/1975 | Bonaparte et al. ................. 252/536 |
| 4,092,438 | 5/1978 | Tonner ................................ 422/658 |
| 4,287,082 | 9/1981 | Tolfo et al. ..................... 252/174.12 |
| 4,318,818 | 3/1982 | Letton et al. ................... 252/174.12 |

FOREIGN PATENT DOCUMENTS

1354761 5/1974 United Kingdom .

OTHER PUBLICATIONS

Moore, W. J., *Physical Chemistry*, N.J., Prentice-Hall, 1972, pp. 449–461.

*Primary Examiner*—Michael S. Marcus
*Attorney, Agent, or Firm*—Charles J. Zeller

[57] ABSTRACT

Aqueous enzyme preparation stabilized with a salt of a lower molecular weight acid in the presence of alcohol.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-19 are cancelled.

* * * * *